US012605337B2

(12) United States Patent
Sun et al.

(10) Patent No.: US 12,605,337 B2
(45) Date of Patent: Apr. 21, 2026

(54) NANOPARTICLE DRUG TARGETING JFK AND USE THEREOF

(71) Applicant: Peking University, Beijing (CN)

(72) Inventors: Luyang Sun, Beijing (CN); Zhaofei Liu, Beijing (CN); Lin He, Beijing (CN); Yongfeng Shang, Beijing (CN); Chao Gao, Beijing (CN); Shimiao Yu, Beijing (CN)

(73) Assignee: Peking University, Beijing (CN)

( * ) Notice: Subject to any disclaimer, the term of this patent is extended or adjusted under 35 U.S.C. 154(b) by 174 days.

(21) Appl. No.: 18/763,256

(22) Filed: Jul. 3, 2024

(65) Prior Publication Data

US 2025/0009662 A1     Jan. 9, 2025

(30) Foreign Application Priority Data

Jul. 5, 2023     (CN) .......................... 202310813522.2

(51) Int. Cl.
| | |
|---|---|
| *A61K 9/1272* | (2025.01) |
| *A61K 9/51* | (2006.01) |
| *A61K 31/713* | (2006.01) |
| *A61K 38/02* | (2006.01) |
| *C12N 15/113* | (2010.01) |

(52) U.S. Cl.
CPC .......... *A61K 9/1272* (2013.01); *A61K 9/5123* (2013.01); *A61K 9/5192* (2013.01); *A61K 31/713* (2013.01); *A61K 38/02* (2013.01); *C12N 15/1137* (2013.01)

(58) Field of Classification Search
CPC .. A61K 9/1272; A61K 9/5123; A61K 9/5192; A61K 31/713; A61K 38/02; C12N 15/1137
See application file for complete search history.

*Primary Examiner* — Trevor Love
(74) *Attorney, Agent, or Firm* — Calderon Safran & Wright PC; Corinne Marie Pouliquen

(57)     ABSTRACT

A nanoparticle drug based on a small interfering RNA (siRNA) targeting JFK and use thereof are provided. Nucleotide sequences of the sense strand and the antisense strand of the siRNA targeting JFK are set forth in SEQ ID NO: 1 and SEQ ID NO: 2, respectively. Liposomes can be used to encapsulate the complex of the siRNA and a protamine to produce a nanoparticle drug targeting JFK, which may be used to treat a disease related to abnormally-high expression of JFK. In this disclosure, breast cancer 4T1 cell-based tumor-bearing mice serve as the model for evaluating the anti-tumor activity of combined therapy involving the nanoparticle drug targeting JFK and radiotherapy. The results reveal that this combined therapy exhibits superior anti-tumor activity compared to the control group.

15 Claims, 10 Drawing Sheets
Specification includes a Sequence Listing.

JFK siRNA
🕂

Protamine

Protamine/JFK siRNA

🕂

(2,3-dioleoyl-propyl)-trimethylammonium chloride/cholesterol/polyethylene glycol-2000 liposome Liposomes/Protamine /JFK siRNA JFK siRNA
+

Protamine

Protamine/JFK siRNA (2,3-dioleoyl-propyl)-
trimethylammonium
chloride/cholesterol/
polyethylene glycol-
20000 liposome Liposomes/Protamine
/JFK siRNA

```
                              SEQUENCE LISTING

Sequence total quantity: 6
SEQ ID NO: 1              moltype = RNA  length = 21
FEATURE                  Location/Qualifiers
source                   1..21
                         mol_type = other RNA
                         note = Sense strand of JFK siRNA 3
                         organism = synthetic construct
SEQUENCE: 1
attctcaatg gtggaaattt t                                        21

SEQ ID NO: 2              moltype = RNA  length = 21
FEATURE                  Location/Qualifiers
source                   1..21
                         mol_type = other RNA
                         note = Antisense strand of JFK siRNA 3
                         organism = synthetic construct
SEQUENCE: 2
aatttccacc attgagaatt t                                        21

SEQ ID NO: 3              moltype = RNA  length = 21
FEATURE                  Location/Qualifiers
source                   1..21
                         mol_type = other RNA
                         note = Sense strand of JFK siRNA 1
                         organism = synthetic construct
SEQUENCE: 3
tagacattaa agacaccaat t                                        21

SEQ ID NO: 4              moltype = RNA  length = 21
FEATURE                  Location/Qualifiers
source                   1..21
                         mol_type = other RNA
                         note = Antisense strand of JFK siRNA 1
                         organism = synthetic construct
SEQUENCE: 4
ttggtgtctt taatgtctat t                                        21

SEQ ID NO: 5              moltype = RNA  length = 21
FEATURE                  Location/Qualifiers
source                   1..21
                         mol_type = other RNA
                         note = Sense strand of JFK siRNA 2
                         organism = synthetic construct
SEQUENCE: 5
ctgtccagga aggaaacatt t                                        21

SEQ ID NO: 6              moltype = RNA  length = 21
FEATURE                  Location/Qualifiers
source                   1..21
                         mol_type = other RNA
                         note = Antisense strand of JFK siRNA 2
                         organism = synthetic construct
SEQUENCE: 6
atgtttcctt cctggacagt t                                        21
```

1

NANOPARTICLE DRUG TARGETING JFK AND USE THEREOF

CROSS REFERENCE TO RELATED APPLICATION

This patent application claims the benefit and priority of Chinese Patent Application No. 202310813522.2 filed with the China National Intellectual Property Administration on Jul. 5, 2023, the disclosure of which is incorporated by reference herein in its entirety as part of the present application.

REFERENCE TO SEQUENCE LISTING

A computer readable XML file entitled "GWP20240402800_seqlist", that was created on May 31, 2024, with a file size of about 7,272 bytes, contains the sequence listing for this application, has been filed with this application, and is hereby incorporated by reference in its entirety.

TECHNICAL FIELD

The present disclosure belongs to the technical field of biomedicine, and in particular relates to a nanoparticle drug targeting JFK and use thereof.

BACKGROUND

JFK is a human Kelch domain-containing F-BOX protein and serves as an important E3 ubiquitin ligase. Through the generation of SKP1-CUL1-F-BOX (SCF) complex, JFK mediates the proteasome-dependent degradation of various important molecules including p53, ING4, and ING5. Thus, JFK plays an important role in biological behaviors such as occurrence and development of breast cancer, angiogenesis and metastasis of breast cancer, regulation of adipocyte differentiation and lipogenesis, osteogenic differentiation, and skeletal development. JFK is expressed at an abnormally-high level in a variety of diseases such as breast cancer, metabolic syndrome-associated obesity and nonalcoholic fatty liver disease, osteodysplasty, and osteoporosis. However, there are currently no JFK-targeted drugs for treating these diseases.

Small interfering RNA (siRNA), a class of double-stranded RNA that is 20 to 25 nucleotides in length, can induce the cleavage and degradation of mRNAs for specific genes to inhibit the expression of these genes at a transcriptional level. Compared with antibody drugs and small-molecule drugs, siRNA drugs have advantages such as convenient synthesis, high specificity, and short development cycle. siRNA drugs were first approved by the Food and Drug Administration (FDA) in 2018 for the treatment of peripheral neuropathy caused by hereditary transthyretin amyloidosis (hATTR). However, siRNAs are easily degraded by nucleases due to their structural instability, which limits the use of siRNAs in vivo. Therefore, it is crucial to develop a targeted siRNA drug delivery system that can efficiently and safely deliver siRNAs to specific organs or tissues for the research and development as well as application of siRNA drugs.

Liposomes are spherical lipid bilayers each with a diameter of 50 nm to 1,000 nm, and have flexible lipid compositions. They can be prepared into various types of nanoparticle drug carrier systems with different sizes and surface characteristics, which have the advantages of, e.g., convenient drug delivery, high delivery efficiency, small rejection, strong stability, and long-term sustained release. The cationic liposome DOTAP is a widely-used non-viral vector, which can encapsulate nucleic acid molecules such as siRNA molecules in a lipid bilayer to protect the RNA from degradation and deliver the RNA to a target site.

The radiotherapy refers to a method of treating tumors using high-energy ionizing radiation to kill cancer cells, alongside surgery and drug therapy as the three major approaches for cancer treatment. About 70% of tumor patients need to undergo radiotherapy at different stages of the disease. However, as the tumor volume increases, becomes more hypoxic, and exhibits increased heterogeneity, the sensitivity of the tumor to radiotherapy gradually decreases, leading to so called radiotherapy resistance. Therefore, the development of a drug that can enhance the sensitivity of the tumor to radiotherapy is of vital importance for tumor treatment.

SUMMARY

In view of the problems in the prior art, an objective of the present disclosure is to provide a siRNA targeting JFK and use thereof. A liposome can be used to encapsulate a complex of the siRNA and a protamine to produce a nanoparticle drug targeting JFK, which may be used to treat diseases related to abnormally-high expression of JFK. The nanoparticle drug, when used in combination with radiotherapy, may significantly enhance the sensitivity of the tumor to radiotherapy.

The objective of the present disclosure is allowed by the following technical solutions.

In a first aspect, the present disclosure provides a siRNA targeting JFK, where the siRNA has a sense strand with the nucleotide sequence of SEQ ID NO: 1 and an antisense strand with the nucleotide sequence of SEQ ID NO: 2.

In a second aspect, the present disclosure provides use of the siRNA in the preparation of a drug for treating a disease related to abnormally-high expression of JFK.

In some embodiments, the disease related to abnormally-high expression of JFK includes breast cancer, metabolic syndrome-associated obesity and nonalcoholic fatty liver disease, osteodysplasty, and osteoporosis.

In a third aspect, the present disclosure provides a nanoparticle drug targeting JFK, where the nanoparticle drug is produced by encapsulating a complex of the siRNA and a protamine with a liposome; and the siRNA has a sense strand with the nucleotide sequence of SEQ ID NO: 1 and an antisense strand with the nucleotide sequence of SEQ ID NO: 2.

In some embodiments, the liposome is a cationic liposome selected from the group consisting of trimethyl-2,3-dioleyloxypropylammonium chloride and trimethyl-2,3-dioleyloxypropylammonium bromide.

In some embodiments, the liposome, the siRNA, and the protamine in the nanoparticle drug are in a mass ratio of (1-8): 1:1.

In some embodiments, the nanoparticle drug has an average diameter of 50 nm to 150 nm and a potential of 5 mV to 15 mV.

In a fourth aspect, the present disclosure provides a method of preparing the nanoparticle drug targeting JFK, including the following steps:

step 1, preparation of an outer liposomal membrane:
taking, thoroughly mixing, and completely dissolving (2,3-dioleoyl-propyl)-trimethyl chloride (DOTAP), cholesterol, and polyethylene glycol (polyethylene glycol (PEG)-2000) according to a specified ratio, preparing a resulting mixture into a liposomal film with a uniform thickness by a rotary evaporator, dissolving the liposomal film with diethyl pyrocarbonate (DEPC)-treated water until the liposomal film is completely hydrated, and extruding the hydrated liposomal film by an extruder die to obtain the outer liposomal membrane; and step 2, encapsulation of the complex:

conducting a first incubation of the siRNA and the protamine at room temperature, adding the outer liposomal membrane prepared in step 1 to the incubated siRNA and protamine, and conducting a second incubation at room temperature to obtain the nanoparticle drug targeting JFK.

In a fifth aspect, the present disclosure provides use of the siRNA in the preparation of a drug for treating a disease related to abnormally-high expression of JFK.

In some embodiments, the disease related to abnormally-high expression of JFK includes breast cancer, metabolic syndrome-associated obesity and nonalcoholic fatty liver disease, osteodysplasty, and osteoporosis.

In a sixth aspect, the present disclosure provides use of the nanoparticle drug targeting JFK as a drug delivery carrier. The nanoparticle drug targeting JFK can also be used in combination with another drug including an internal radiation drug (such as $^{177}$Lu), a chemotherapeutic drug, or a targeted drug.

Compared with the prior art, the embodiments of the present disclosure has the following beneficial effects:

1. The siRNA targeting JFK of the present disclosure may effectively inhibit the transcription of JFK, thereby reducing the production of JFK from the root. The siRNA may be used to prepare a drug for treating diseases related to abnormally-high expression of JFK. The application of the drug may result in a more potent therapeutic effect for such diseases.

2. In the nanoparticle drug targeting JFK of the present disclosure, a liposomal nanoparticle is adopted as a carrier to deliver the siRNA targeting JFK to a lesion site, which improves the drug delivery efficiency, reduces the synthesis cost, and improves the stability of the drug in vivo in terms of an inhibitor targeting the protein.

3. The nanoparticle drug targeting JFK of the present disclosure has a prominent anti-tumor effect in vivo, and may significantly enhance the sensitivity of a tumor with high JFK expression to traditional radiotherapy when used in combination with the traditional radiotherapy.

BRIEF DESCRIPTION OF THE DRAWINGS

The present disclosure is described in further detail below with reference to the accompanying drawings and examples.

DETAILED DESCRIPTION OF THE EMBODIMENTS

In the following examples, the devices and raw materials involved are commercially available unless otherwise specified.

The raw materials are shown in Table 1.

TABLE 1

| Reagent name | Source |
| --- | --- |
| DOTAP | AVT |
| Cholesterol | Sigma-Aldrich |
| PEG-2000 | Sigma-Aldrich |
| Protamine | Sigma-Aldrich |
| JFK siRNA-Cy5 | GenePharma |

The devices are shown in Table 2.

TABLE 2

| Device name | Source |
| --- | --- |
| Rotary evaporator | EYELA (EYEL4 N-1300) |
| Liposome extruder | AVT |
| Transmission electron microscope | JEOL (JEM-1400) |
| Confocal microscope | ZEISS (LSM880) |
| Dynamic light scattering instrument | Malvern (ZETASIZER NANO ZSP) |
| Freezing microtome | Leica (CM3050S) |
| In vivo small animal imager | PerkinElmer (IVIS Lumina Series III) |

Example 1

Figure 1:
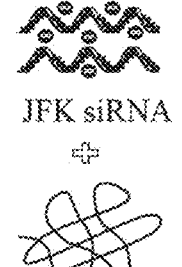
FIG. 1 is a schematic diagram of the structure and preparation process of the nanoparticle drug targeting JFK in Example 1.
Figure 1:
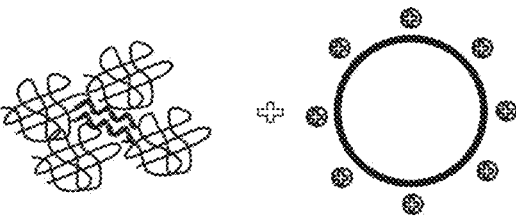
Figure 1:
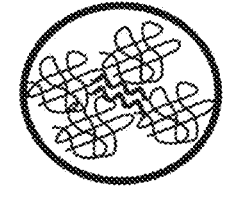

As shown in FIG. 1, this example provides a siRNA targeting JFK. The nucleotide sequence of the siRNA's sense strand is set forth in SEQ ID NO: 1:

5'-AUUCUCAAUGGUGGAAAUUTT-3'; and the nucleotide sequence of the siRNA's antisense strand is set forth in SEQ ID NO: 2:

5'-AAUUUCCACCAUUGAGAAUTT-3'.

Further, in this example, a nanoparticle drug targeting JFK was prepared with the siRNA as follows:

Step 1, Preparation of the Outer Liposomal Membrane:

According to a molar ratio of 1:1:1, (2,3-dioleoyl-propyl)-trimethyl chloride (DOTAP), cholesterol, and PEG-2000 were taken, thoroughly mixed, and completely dissolved. A resulting mixture was prepared into a liposomal film with a uniform thickness by a rotary evaporator. The liposomal film was dissolved with 1 mL of DEPC-treated water until the liposomal film was completely hydrated. The hydrated liposomal film was extruded by an extruder 15 to 20 times with each of 200 nm and 100 nm dies to obtain the outer liposomal membrane.

Step 2, Encapsulation of the Complex:

The siRNA described in this example and the protamine were incubated at room temperature for 10 min. The outer liposomal membrane prepared in the step 1 was added to the incubated mixture, followed by another incubation at room temperature for 10 min to obtain the nanoparticle drug targeting JFK (namely, an LPR nanoparticle drug). The siRNA, the protamine, and the outer liposomal membrane were in a mass ratio of 1:1:1.

Comparative Example 1

In this comparative example, an empty liposome (excluding the protamine) was prepared as follows:

According to a molar ratio of 1:1:1, (2,3-dioleoyl-propyl)-trimethyl chloride (DOTAP), cholesterol, and PEG-2000 were taken, thoroughly mixed, and completely dissolved. A resulting mixture was prepared into a liposomal film with a uniform thickness by a rotary evaporator. The liposomal film was dissolved with 1 mL of DEPC-treated water until the liposomal film was completely hydrated. The hydrated liposomal film was extruded by an extruder 15 to 20 times with each of 200 nm and 100 nm dies to obtain an outer liposomal membrane (namely, the empty liposome).

Test Example 1

In order to determine the physical and chemical properties of the nanoparticle drug targeting JFK prepared in Example 1, the particle size, potential, morphology, and stability of the nanoparticle drug each were determined in this test example. The particle sizes and zeta potentials of the empty liposome and the JFK siRNA-loaded nanoparticle drug targeting JFK prepared by the methods in Comparative Example 1 and Example 1 respectively were detected by a dynamic light scattering instrument. The morphological characteristics of liposomal nanoparticles were observed by a transmission electron microscope.

Figure 2A:
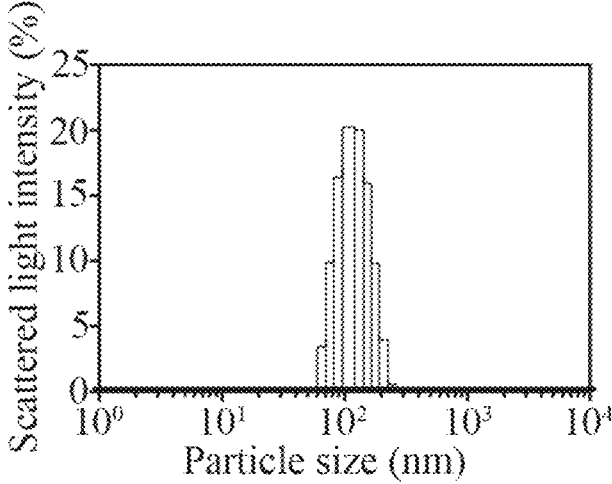
FIGS. 2A-2H show physical and chemical properties of the nanoparticle drug targeting JFK in Test Example 1.
Figure 2B:
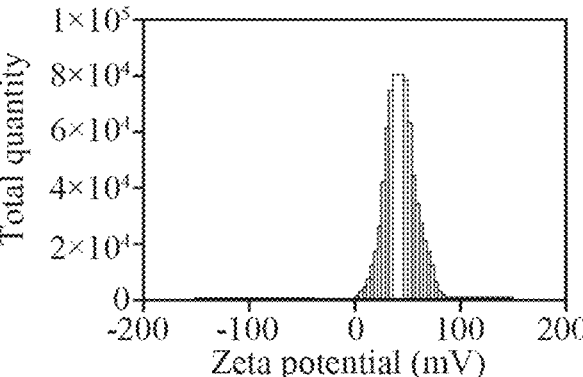
Figure 2C:
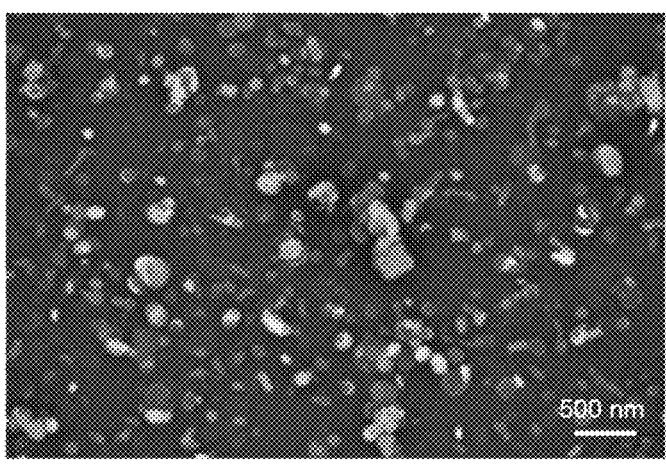
Figure 2D:
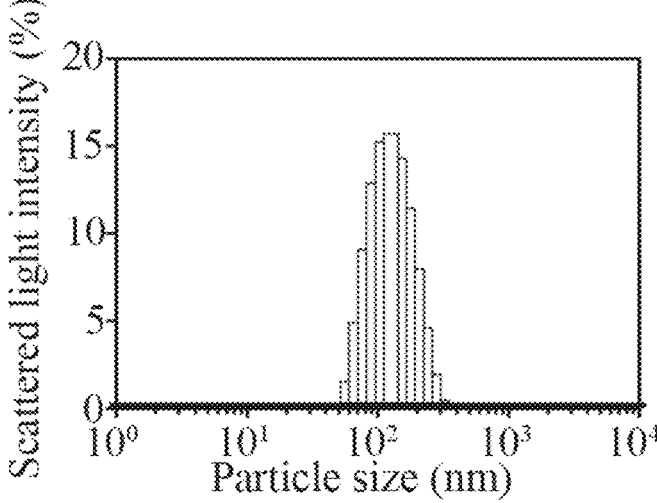
Figure 2E:
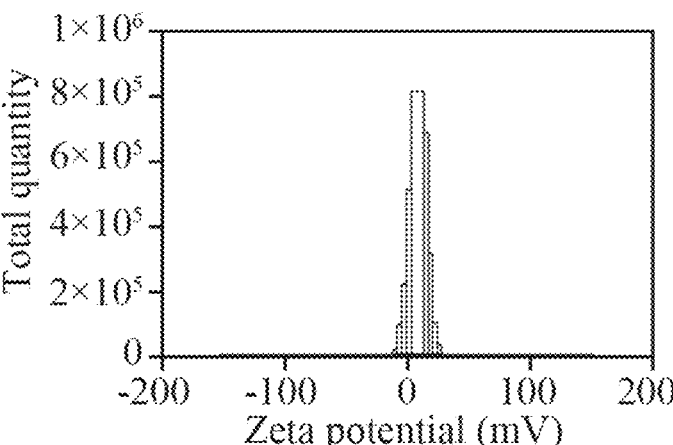

Results of this test example showed that the empty liposome in Comparative Example 1 had a particle size of about 108 nm (FIG. 2A) and a potential of about 40 mV (FIG. 2B). Electron microscopy results revealed that the empty liposome had a uniform particle size (FIG. 2C). The empty liposome was loaded with JFK siRNA to produce the nanoparticle drug targeting JFK in Example 1. The nanoparticle drug targeting JFK had a particle size of about 120 nm (FIG. 2D) and a potential of about 10 mV (FIG. 2E). Electron microscopy results showed that the morphology of the empty liposome did not change significantly after the empty liposome was loaded with the siRNA (FIG. 2F).

In order to further detect the stability of the nanoparticle drug in Example 1, the particle size of the nanoparticle drug and the binding affinity of the siRNA in the liposome were characterized. Particle sizes of the nanoparticle drug targeting JFK at different time points were detected by a dynamic scattering instrument. Binding affinity of the siRNA at different time points were detected by agarose gel electrophoresis, where agarose with a concentration of 2% (mass/volume) was prepared for electrophoresis at a voltage of 100 V for 20 min, followed by analysis under ultraviolet irradiation.

Figure 2F:
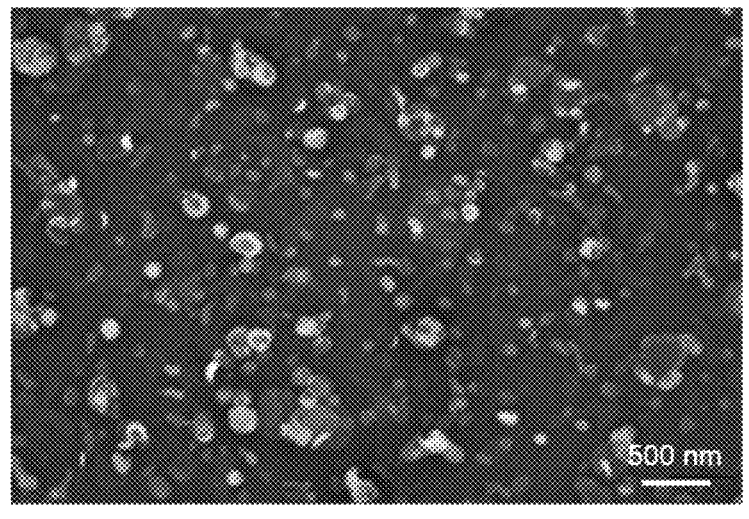
Figure 2G:
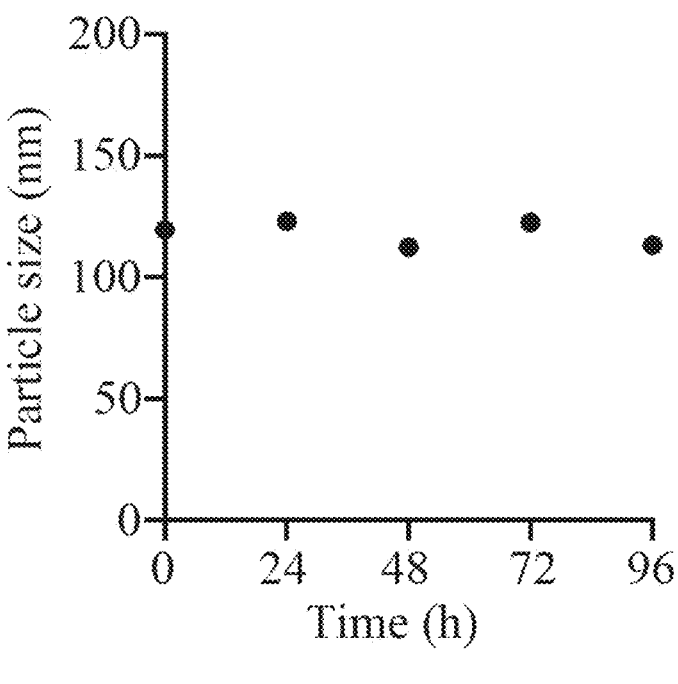
Figure 2H:
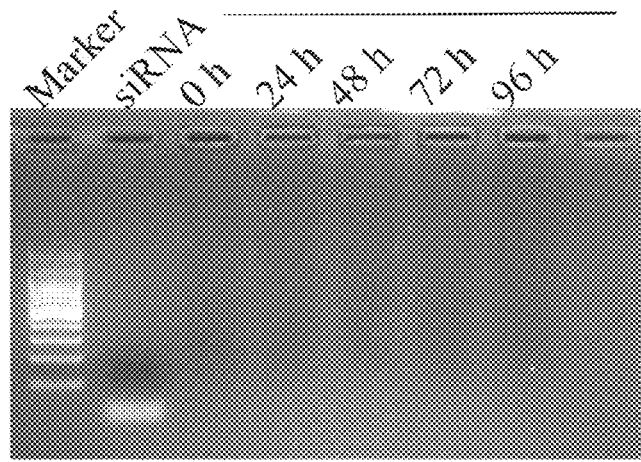

Particle size test results showed that the particle size of the LPR nanoparticle drug in Example 1 remained stable, with no significant change over a period of 96 h (FIG. 2F). Electrophoretic mobility shift assay (EMSA) results indicated that the siRNA maintained an excellent binding affinity in the liposome within 96 h (FIG. 2H).

Test Example 2

In this test example, the siRNA targeting JFK (Cy5-JFK siRNA) in Example 1 was labeled with a fluorescent dye Cy5, and then the Cy5-labeled LPR nanoparticle drug was prepared with reference to the method in Example 1.

The intervention effect of the LPR nanoparticle drug on the expression of JFK in 4T1 cells in vitro was detected. This included subcellular distribution of the drug and changes in the JFK level in 4T1 cells at different time points after administration.

Figure 3A:
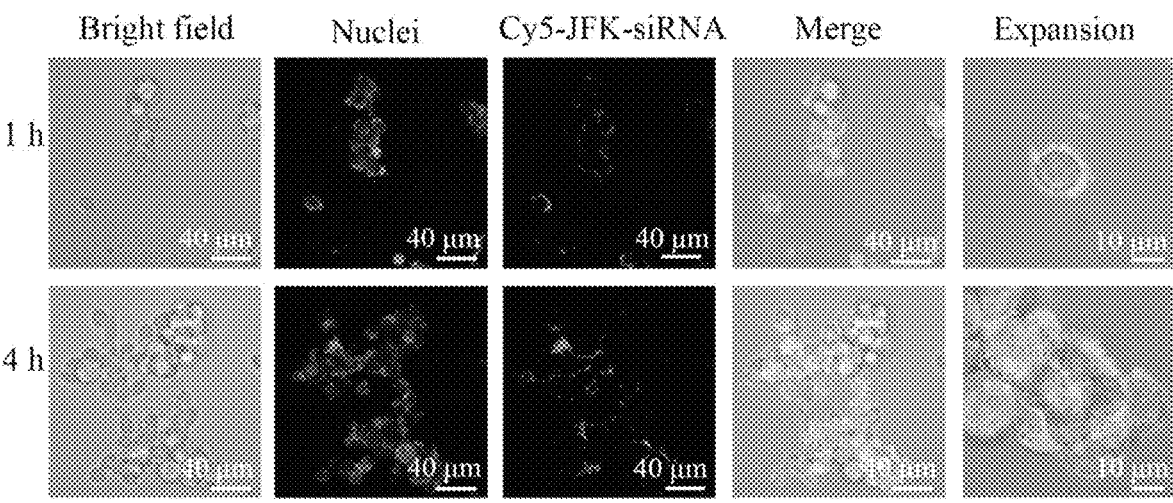
FIGS. 3A-3C show detection results of the intervention effect of the nanoparticle drug targeting JFK on JFK expression in breast cancer 4T1 cells in vitro in Test Example 2.

4T1 cells were incubated for 24 h until a confluency of about 50% to 60%. The Cy5-labeled LPR nanoparticle drug prepared above was added to the cells. The cells were further incubated, during which the Cy5 fluorescence expression in the cells was observed by a confocal microscope at 1 h and 4 h. Results showed that the drug effectively entered the 4T1 cells at 1 h and 4 h after the treatment with the LPR nanoparticle drug carrying Cy5-JFK siRNA, and the amount of the drug entering the cells increased with the increase of the time of treatment (FIG. 3A).

Figure 3B:
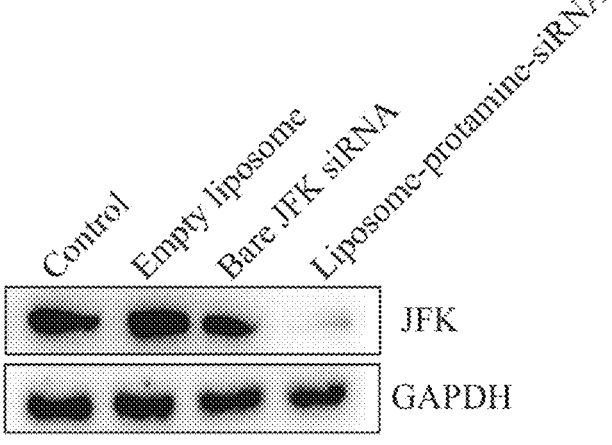

4T1 cells were incubated for 24 h until a confluency of about 50% to 60%. The empty liposome, the bare Cy5-JFK siRNA, and the Cy5-labeled LPR nanoparticle drug each were added to the cells, and the cells were further incubated for 48 h. Western blotting and immunofluorescence staining tests were conducted to observe the expression of JFK. The specific method of the western blotting test was as follows: total protein was extracted by an RIPA lysis solution from 4T1 cells undergone different treatments. The 10% poly-acrylamide gel electrophoresis was conducted for 60 min, followed by transfer for 90 min, and a corresponding membrane was blocked for 60 min. The membrane was incubated with a JFK primary antibody (1:2,000) at 4° C. overnight. After washing, it was further incubated with the secondary antibody for 2 h, followed by washing, exposure for observation. It was shown that the treatment with the LPR nanoparticle drug carrying Cy5-JFK siRNA significantly reduced the expression level of JFK, as compared with the control group, the empty liposome group, and the bare Cy5-JFK siRNA group (FIG. 3B).

Figures 3C, 4A:
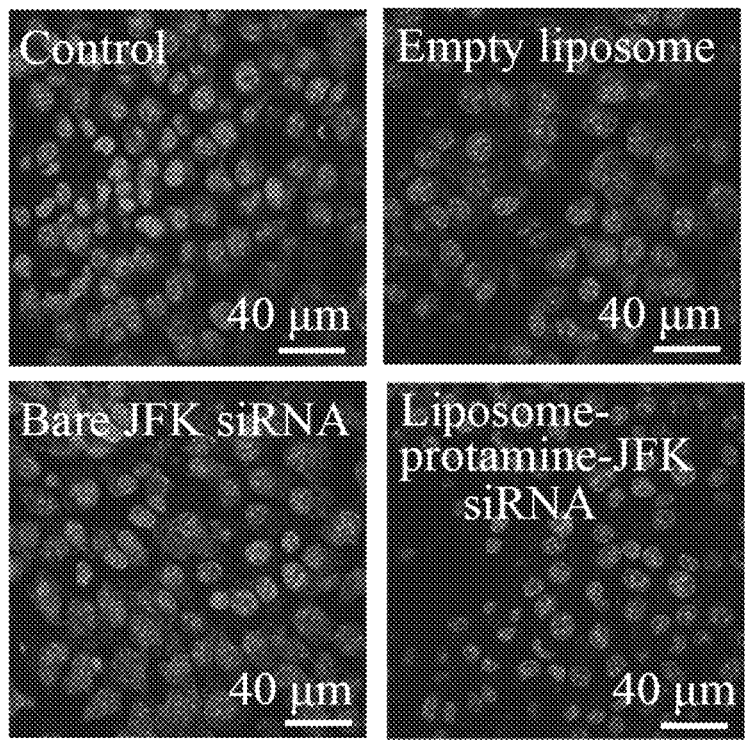
FIGS. 4A-4B show evaluation results of the tumor-targeted delivery effect of the nanoparticle drug targeting JFK in mice in Test Example 3.

The specific method of the immunofluorescence staining test was as follows. The 4T1 cells subjected to different treatments each were fixed with 4% paraformaldehyde for 10 min, blocked with 1% bovine serum albumin for 1 h, and incubated with a primary antibody JFK (1:200) at 4° C. overnight. After washing, the cells were incubated with a secondary antibody (1:200) at room temperature for 2 h, then washed, and incubated with a 4',6-diamidino-2-phe-nylindole (DAPI) dye for 10 min. The cells were mounted, and then observed by a confocal microscope. It was revealed that the treatment with the LPR nanoparticle drug carrying Cy5-JFK siRNA could significantly reduce the expression level of JFK compared with the control group, the empty liposome group, and the bare Cy5-JFK siRNA group (FIG. 3C).

Test Example 3

In this test example, the delivery effect of the Cy5-labeled LPR nanoparticle drug prepared in Test Example 2 in 4T1 tumor-bearing mice was evaluated. This involved distributions of the drug in different organs and tissues and in vivo knock-down efficiency of JFK after administration. Specifically:

In this test example, the empty liposome, the bare JFK siRNA, and the Cy5-JFK siRNA-loaded liposome (the LPR group) each were injected once into mice (1 μg/10 g mice) through tail vein, and 24 h later, the distributions of each drug in various organs and tumors of mice were characterized by an in vivo small animal imaging test system.

Figure 4B:
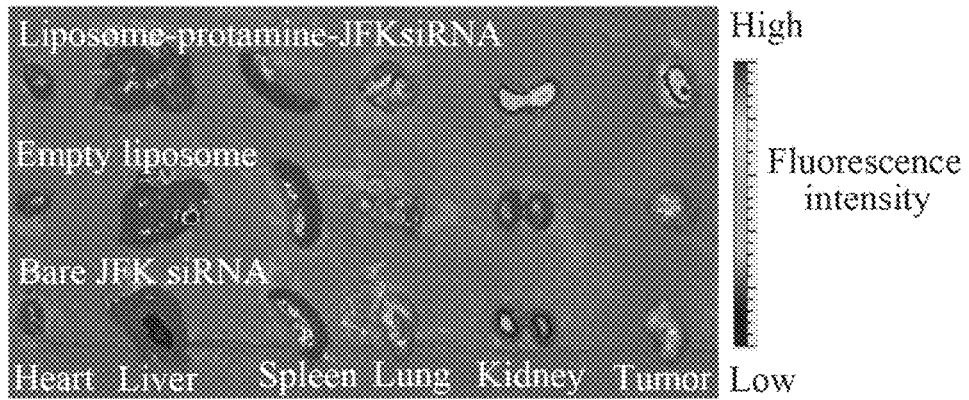

In vivo imaging results indicated that the fluorescence of Cy5 could be observed at the tumor site in the LPR group compared with the other 2 groups (FIG. 4A). Ex vitro test results showed that, in contrast to the group injected with the liposome or the JFK siRNA alone, in the group injected with the LPR nanoparticle drug, most of the JFK LPR nanoparticle drug was successfully introduced into tumors in mice except that a small amount of the JFK LPR nanoparticle drug retained in kidneys due to metabolism (FIG. 4B).

Test Example 4

In this test example, the anti-tumor effects of the LPR nanoparticle drug prepared in Example 1 were evaluated by intratumoral injection in 4T1 tumor-bearing mice in combination with radiotherapy, including the anti-tumor effect of the LPR nanoparticle drug alone and the effect of the combining LPR nanoparticle drug with radiotherapy compared with the radiotherapy alone.

Figure 5A:
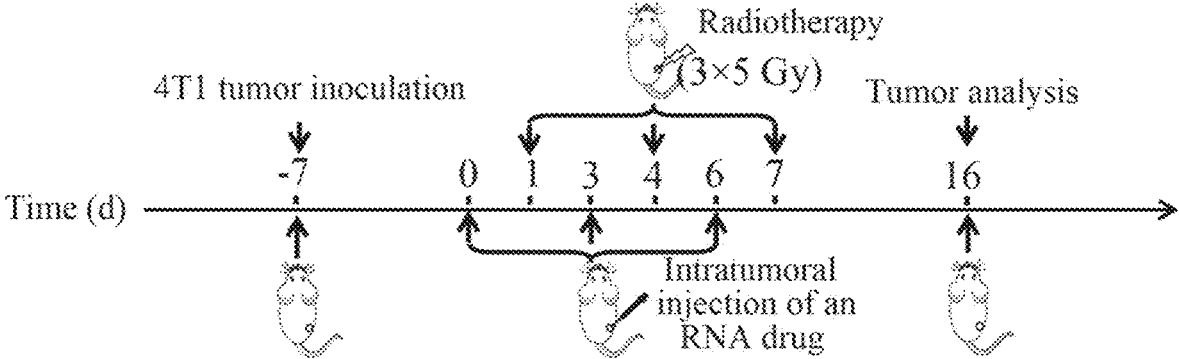
FIGS. 5A-5E show evaluation results of therapeutic effects of the nanoparticle drug targeting JFK, a radiotherapy, and a combined therapy of the nanoparticle drug and the radiotherapy for tumors in mice in Test Example 4 (the nanoparticle drug is intratumorally injected)
Figure 5B:
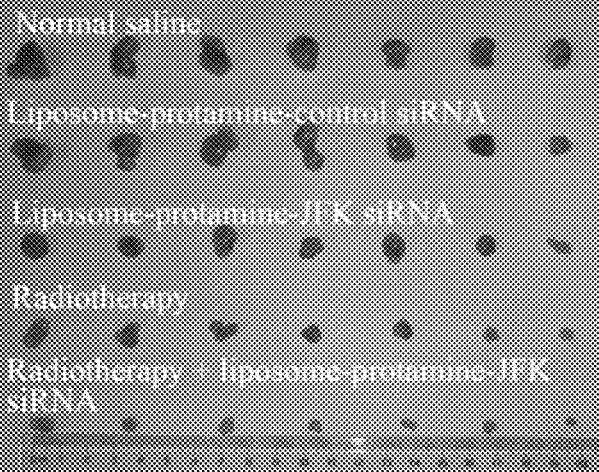
Figure 5C:
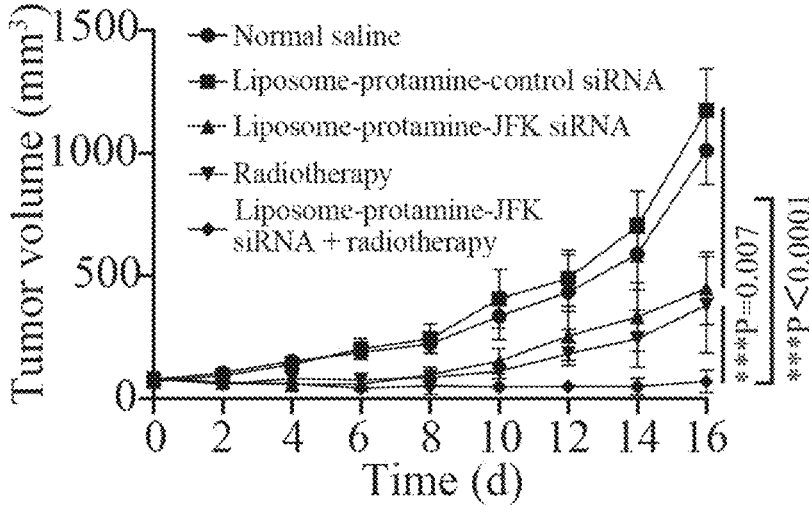
Figure 5D:
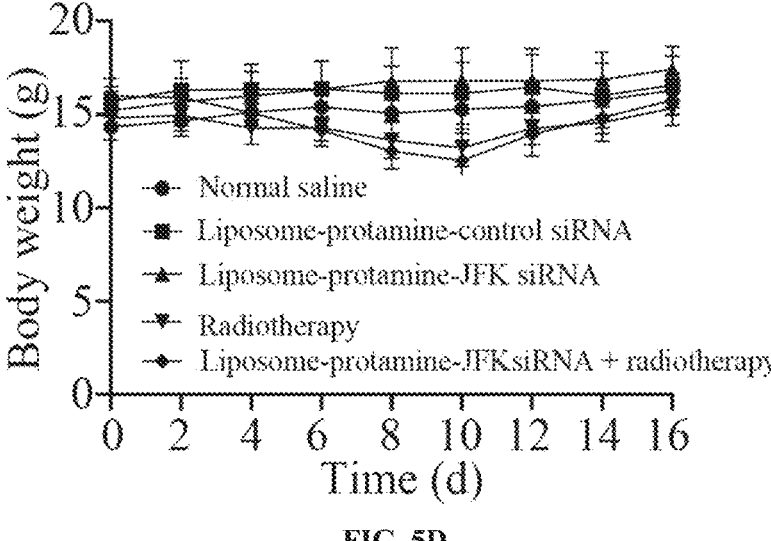
Figure 5E:
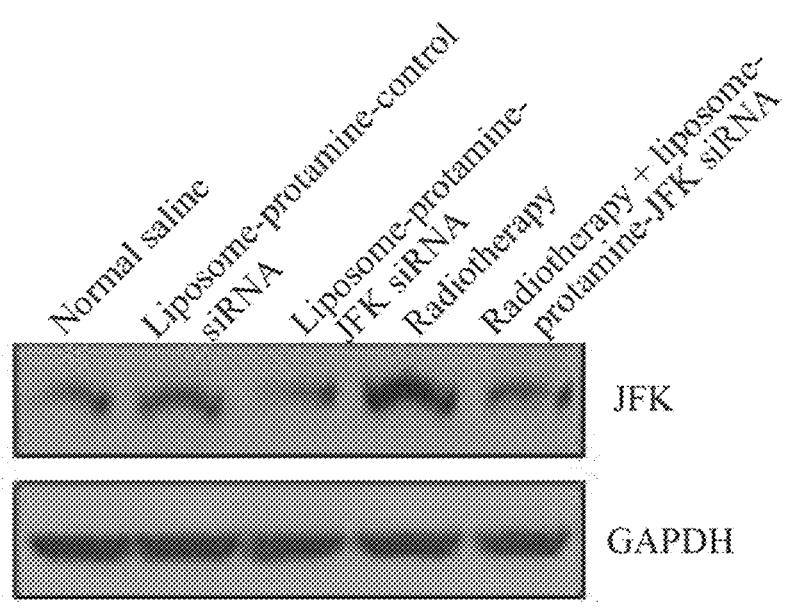

4T1 tumor-bearing mouse model was established 7 d before administration. The mice were divided into 5 groups, including a negative control group receiving normal saline, a liposome-protamine-control siRNA (blank control siRNA) group, a liposome-protamine-JFK siRNA (LPR group), a radiotherapy (RT) group, and a combined therapy group of LPR+RT. On days 0, 3, and 6, the LPR nanoparticle drug (or the empty liposome or the liposome-protamine-control siRNA (blank control siRNA group) was administered through intratumoral injection. On days 1, 4, and 7, the radiotherapy was applied with 3×5 Gy (Gray unit, a standard unit of measurement for the absorption of ionizing radiation energy, and 1 Gray is equal to 1 joule of energy absorbed per killogram an material being irradiated (1 Gy=1 J/kg)). On day 16, tumors were collected for testing (FIG. 5A).
The Test Results Showed that:

Compared with mice in the negative control group, mice in the LPR group had a significant reduction in tumor-bearing volume (FIG. 5B and FIG. 5C), with no change in body weight (FIG. 5D), and a significant decrease in JFK expression levels in tumor cells (FIG. 5E).

Compared with mice in the RT group, mice in the LPR+RT group exhibited a significant reduction in tumor-bearing volume (FIG. 5B and FIG. 5C), with no change in body weight (FIG. 5D), and a significant decrease in JFK expression level in tumor cells (FIG. 5E).

Therefore, findings indicate that the intratumoral injection of the LPR nanoparticle drug targeting JFK used in the present disclosure has a significant anti-tumor effect, and it enhances the sensitivity of the tumor to radiotherapy when used in combination with radiotherapy.

Test Example 5

In this test example, the anti-tumor effects of the LPR nanoparticle drug prepared in Example 1 were systematically injected through tail vein into 4T1 tumor-bearing mice in combination with radiotherapy, including the anti-tumor effect of the LPR nanoparticle drug alone and the sensitization effect of the combined therapy of the LPR nanoparticle drug and the radiotherapy compared with the radiotherapy alone.

Figure 6A:
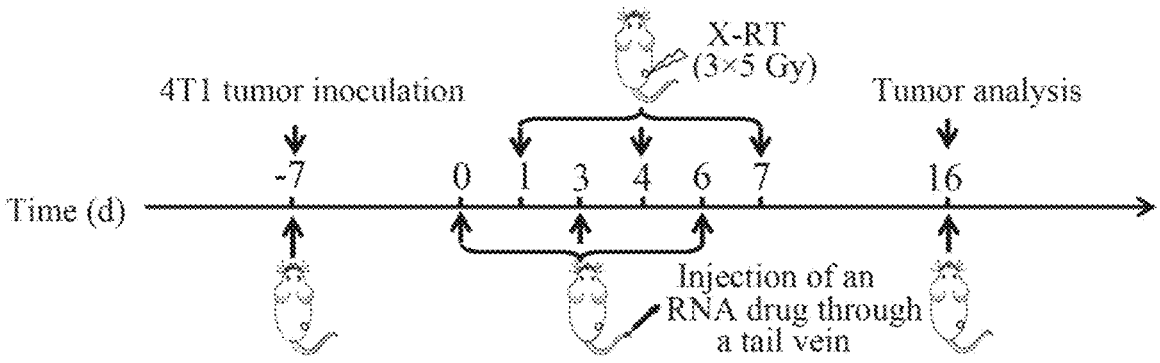
FIGS. 6A-6E show evaluation results of therapeutic effects of the nanoparticle drug targeting JFK, a radiotherapy, and a combined therapy of the nanoparticle drug and the radiotherapy for tumors in mice in Test Example 5 (the nanoparticle drug is systematically injected)
Figure 6B:
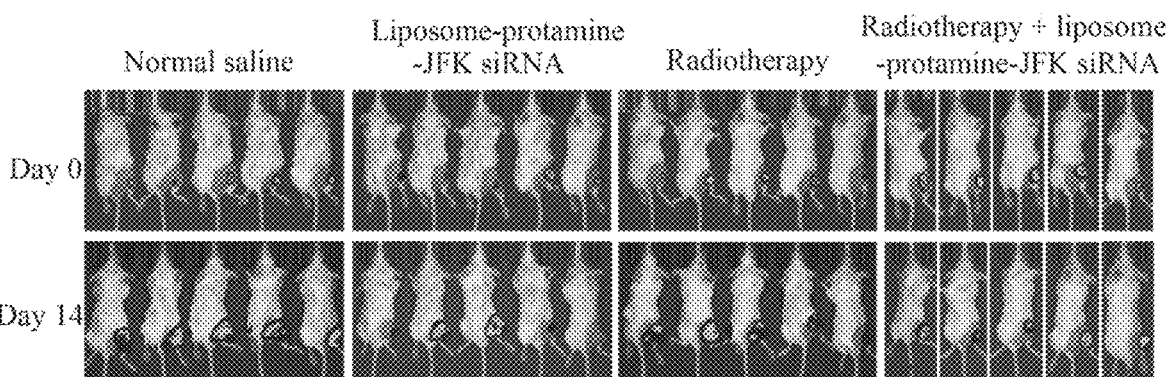
Figure 6C:
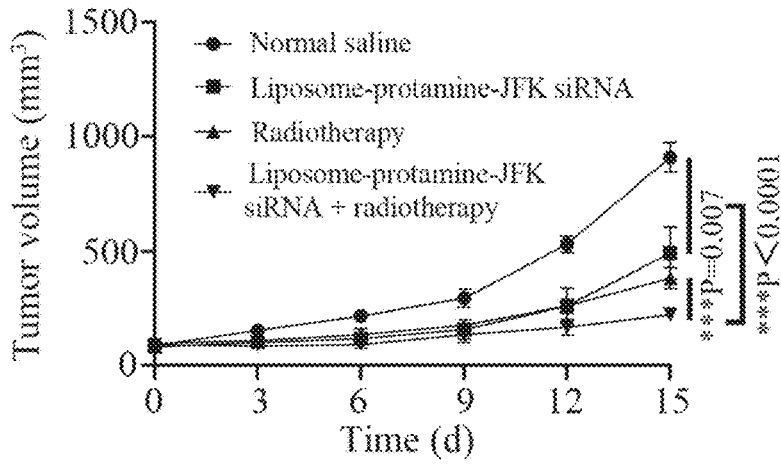
Figure 6D:
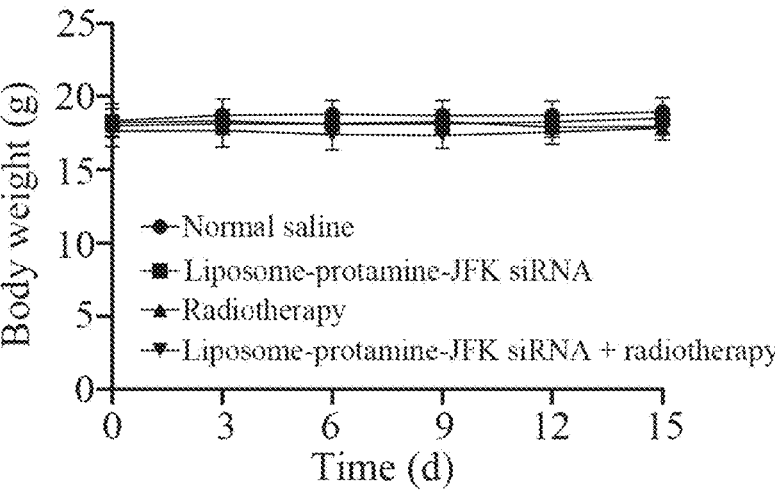
Figure 6E:
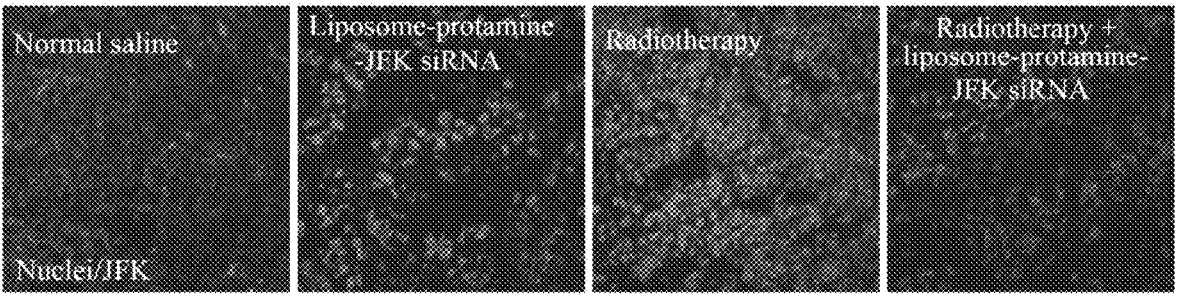

4T1 tumor-bearing mouse model was established 7 d before administration. The mice were divided into 4 groups, including a control group receiving normal saline, a liposome-protamine-JFK siRNA (LPR) group, a radiotherapy (RT) group, and a combined therapy group of LPR+RT. On days 0, 3, and 6, the LPR nanoparticle drug was injected through tail vein. On days 1, 4, and 7, the radiotherapy was applied with 3×5 Gy. On day 16, tumors were collected for testing (FIG. 6A).
The Test Results Showed that:

Mice in the LPR group exhibited a reduced tumor-bearing volume compared with the negative control group, with no significant difference compared to the RT group. Mice in the LPR+RT group showed significantly lower tumor-bearing volume than those in the LPR and RT groups (FIG. 6B and FIG. 6C). There was no significant difference among the groups in terms of the body weight (FIG. 6D). Immunofluorescence staining results demonstrated that the expression level of JFK in tumor cells of the LPR+RT group was significantly reduced (FIG. 6D and FIG. 6E).

Therefore, these findings indicate that the systematical injection of the LPR nanoparticle drug targeting JFK used in the present disclosure has a specified anti-tumor effect, and may significantly enhance the sensitivity of a tumor to radiotherapy when used in combination with radiotherapy, without causing severe systemic adverse reactions.

Comparative Example 2

4T1 cells were transfected with negative control siRNA and three different JFK siRNA sequences separately (as shown in Table 3). Forty-eight hours later, cells were harvested for qPCR and western blotting.

TABLE 3

| | Nucleotide sequence (5'→3') | SEQ ID NO: |
|---|---|---|
| JFK siRNA1#-sense strand | UAGACAUUAAAGACACCAATT | 3 |
| JFK siRNA1#-antisense strand | UUGGUGUCUUUAAUGUCUATT | 4 |
| JFK siRNA2#-sense strand | CUGUCCAGGAAGGAAACAUTT | 5 |
| JFK siRNA2#-antisense strand | AUGUUUCCUUCCUGGACAGTT | 6 |
| JFK siRNA3#-sense strand | AUUCUCAAUGGUGGAAAUUTT | 1 |
| JFK siRNA3#-antisense strand | AAUUUCCACCAUUGAGAAUTT | 2 |

Figure 7A:
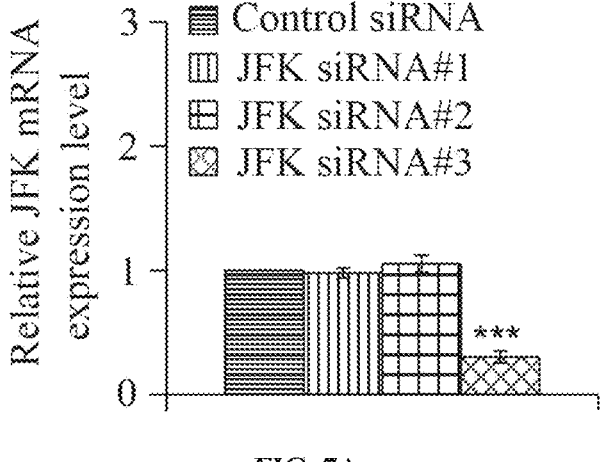
FIGS. 7A-7B are comparison diagrams of detection results of three different JFK siRNA sequences in Comparative Example 2.
Figure 7B:
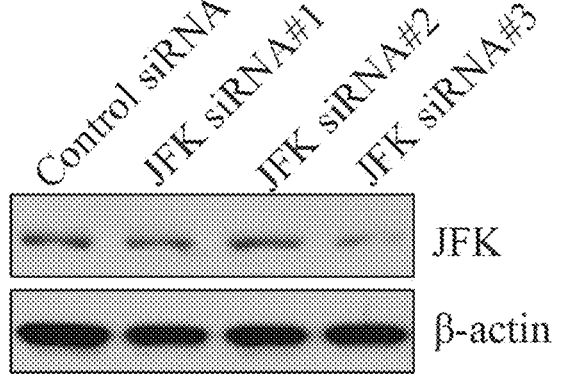

It was observed that, compared with the negative control group (control siRNA), only the #3 JFK siRNA sequence (the sequence shown in SEQ ID NO: 1 and SEQ ID NO: 2) significantly decreased the mRNA (FIG. 7A) and protein expression levels (FIG. 7B) of JFK (***p<0.001). In contrast, the #1 and #2 JFK siRNA sequences had no impact on the mRNA and protein expression levels of JFK, demonstrating the effectiveness and specificity of the JFK siRNA sequence used in the present disclosure.

Finally, it should be noted that the above are merely intended to describe, rather than to limit the embodiments of the present disclosure. Although the present disclosure is described in detail with reference to the preferred embodiments, those of ordinary skill in the art should understand that modifications or equivalent replacements may be made to the embodiments of the present disclosure without departing from the spirit and scope of the present disclosure.

What is claimed is:

1. A small interfering RNA (siRNA) targeting JFK, wherein the siRNA has a sense strand with the nucleotide sequence of SEQ ID NO: 1 and an antisense strand with the nucleotide sequence of SEQ ID NO: 2.

2. A method for treating a disease related to abnormally-high expression of JFK, comprising administering to a subject in need thereof an therapeutically effective amount of a drug comprising the siRNA according to claim 1.

3. The method according to claim 2, wherein the disease related to abnormally-high expression of JFK comprises breast cancer, metabolic syndrome-associated obesity and nonalcoholic fatty liver disease, osteodysplasty, and osteoporosis.

4. The method of claim 2, wherein the drug is produced by encapsulating a complex of a siRNA and a protamine with a liposome; and the siRNA has a sense strand with the nucleotide sequence of SEQ ID NO: 1 and an antisense strand with the nucleotide sequence of SEQ ID NO: 2.

5. The method of claim 4, wherein the liposome is a cationic liposome selected from the group consisting of trimethyl-2,3-dioleyloxypropylammonium chloride and trimethyl-2,3-dioleoyloxypropylammonium bromide.

6. The method of claim 4, wherein the liposome, the siRNA, and the protamine in the drug are in a mass ratio of 1-8:1:1.

7. The method of claim 4, wherein the drug has an average diameter of 50 nm to 150 nm and a zeta potential of 5 mV to 15 mV.

8. A nanoparticle drug targeting JFK, wherein the nanoparticle drug is produced by encapsulating a complex of a siRNA and a protamine with a liposome; and the siRNA has a sense strand with the nucleotide sequence of SEQ ID NO: 1 and an antisense strand with the nucleotide sequence of SEQ ID NO: 2.

9. The nanoparticle drug targeting JFK according to claim 8, wherein the liposome is a cationic liposome selected from the group consisting of trimethyl-2,3-dioleyloxypropylammonium chloride and trimethyl-2,3-dioleoyloxypropylammonium bromide.

10. The nanoparticle drug targeting JFK according to claim 8, wherein the liposome, the siRNA, and the protamine in the nanoparticle drug are in a mass ratio of 1-8:1:1.

11. The nanoparticle drug targeting JFK according to claim 8, wherein the nanoparticle drug has an average diameter of 50 nm to 150 nm and a zeta potential of 5 mV to 15 mV.

12. A method of preparing the nanoparticle drug targeting JFK according to claim 8, comprising the following steps:

step 1, preparation of an outer liposomal membrane:

taking, thoroughly mixing, and completely dissolving (2,3-dioleoyl-propyl)-trimethyl chloride (DOTAP), cholesterol, and polyethylene glycol (PEG-2000) according to a specified ratio until solids, preparing solution resulting mixture into a liposomal film with a uniform thickness by a rotary evaporator, dissolving the liposomal film with DEPC-treated water until the liposomal film is completely hydrated, and extruding the hydrated liposomal film by an extruder die to obtain the outer liposomal membrane; and step 2, encapsulation of a complex:

conducting a first incubation of a siRNA and the protamine at room temperature, adding the outer liposomal membrane prepared in the step 1 to the incubated siRNA and protamine, and conducting a second incubation at room temperature such that the complex of the siRNA and the protamine is encapsulated in the outer liposomal membrane to obtain the nanoparticle drug targeting JFK, wherein the siRNA has a sense strand with the nucleotide sequence of SEQ ID NO: 1 and an antisense strand with the nucleotide sequence of SEQ ID NO: 2.

13. The method of claim 12, wherein the liposome is a cationic liposome selected from the group consisting of trimethyl-2,3-dioleyloxypropylammonium chloride and trimethyl-2,3-dioleoyloxypropylammonium bromide.

14. The method of claim 12, wherein the liposome, the siRNA, and the protamine in the nanoparticle drug are in a mass ratio of 1-8:1:1.

15. The method of claim 12, wherein the nanoparticle drug has an average diameter of 50 nm to 150 nm and a zeta potential of 5 mV to 15 mV.

* * * * *